United States Patent
Ninomiya et al.

(10) Patent No.: US 8,984,684 B2
(45) Date of Patent: Mar. 24, 2015

(54) MAGNETIC RESONANCE IMAGING DEVICE

(75) Inventors: Atsushi Ninomiya, Ome (JP); Masaru Yokoyama, Tokorozawa (JP); Kazuyuki Yanase, Tokyo (JP); Manabu Yanagimoto, Kawasaki (JP); Takeshi Yatsuo, Kashiwa (JP); Hiroyuki Ohzeki, Moriya (JP)

(73) Assignee: Hitachi Medical Corporation, Tokyo (JP)

(*) Notice: Subject to any disclaimer, the term of this patent is extended or adjusted under 35 U.S.C. 154(b) by 18 days.

(21) Appl. No.: 13/811,998

(22) PCT Filed: Jul. 14, 2011

(86) PCT No.: PCT/JP2011/066137
§ 371 (c)(1),
(2), (4) Date: Jan. 24, 2013

(87) PCT Pub. No.: WO2012/043019
PCT Pub. Date: Apr. 5, 2012

(65) Prior Publication Data
US 2013/0184564 A1    Jul. 18, 2013

(30) Foreign Application Priority Data
Sep. 30, 2010  (JP) ................. 2010-222154

(51) Int. Cl.
*A61B 5/055*     (2006.01)
*G01R 33/38*     (2006.01)
*G01R 33/381*    (2006.01)

(52) U.S. Cl.
CPC .......... *A61B 5/0555* (2013.01); *G01R 33/3806* (2013.01); *G01R 33/381* (2013.01)
USPC ............... 5/601; 600/407; 600/415; 324/318; 324/320

(58) Field of Classification Search
CPC ....... A61B 5/0555; A61B 6/00; A61B 6/0457
USPC ........ 600/407; 5/601, 611; 324/318; 378/198
See application file for complete search history.

(56) References Cited

U.S. PATENT DOCUMENTS 5,525,905 A * 6/1996 Mohapatra et al. ........... 324/318
5,842,987 A * 12/1998 Sahadevan .................... 600/407
(Continued)

FOREIGN PATENT DOCUMENTS

JP  61-48712 U     4/1986
JP  03-103234 A    4/1991
(Continued)

OTHER PUBLICATIONS

Japanese Office Action received in Japanese Application No. 2012-536263 dated May 27, 2014.

*Primary Examiner* — Baisakhi Roy
(74) *Attorney, Agent, or Firm* — Mattingly & Malur, P.C.

(57) ABSTRACT

The magnetic resonance imaging device of the present invention includes a gantry and a bed part comprising a top panel, the gantry comprises a circumferential panel covering outer circumference of a tunnel-shaped static magnetic field space, and a front panel having an opening serving as entrance of a bore for the static magnetic field space, this front panel comprises an arc-shaped outer panel extending from an upper part of the opening serving as entrance of the bore to the ground plane via both sides of the opening, and an inner panel disposed inside the outer panel, a portion connecting the outer panel and the inner panel constitutes a top surface protruding forwardly, and the inner panel is formed in a recessed shape with a concave curved surface extending from the top surface to the opening serving as entrance of the bore.

11 Claims, 9 Drawing Sheets

(56) References Cited

U.S. PATENT DOCUMENTS

| | | | |
|---|---|---|---|
| 6,094,760 A * | 8/2000 | Nonaka et al. | 5/601 |
| 2004/0113620 A1* | 6/2004 | Tsuda et al. | 324/320 |
| 2006/0260050 A1* | 11/2006 | Manzione | 5/601 |
| 2008/0267358 A1 | 10/2008 | Hiyama | |
| 2009/0320206 A1* | 12/2009 | Dyreby et al. | 5/611 |
| 2011/0222667 A1* | 9/2011 | Gregerson et al. | 378/198 |
| 2012/0086452 A1* | 4/2012 | Dohata et al. | 324/318 |

FOREIGN PATENT DOCUMENTS

| | | |
|---|---|---|
| JP | 09-299352 A | 11/1997 |
| JP | 2001-008917 A | 1/2001 |
| JP | 2004-329525 A | 11/2004 |
| JP | 1265497 S | 3/2006 |
| JP | 2008-005999 A | 1/2008 |
| JP | 2008-289854 A | 12/2008 |
| JP | 2010-142942 A | 6/2010 |

\* cited by examiner

MAGNETIC RESONANCE IMAGING DEVICE

TECHNICAL FIELD

The present invention relates to a magnetic resonance imaging (henceforth abbreviated as MRI) device (apparatus) for displaying an arbitrary cross section of a subject utilizing nuclear magnetic resonance (henceforth abbreviated as NMR), in particular, such an MRI device as mentioned above, which allows favorable access of an operator to the subject at the time of imaging.

BACKGROUND ART

There are used various shapes of gantry of MRI apparatuses depending on the type of magnetic field used, for example, one for providing a horizontal static magnetic field space in a tunnel-shaped bore, one for providing a perpendicular static magnetic field space between upper and lower magnet units, and so forth, and in any case, examination is performed by inserting a subject into a bore (open-part) of the gantry as an static magnetic field space.

In general, tunnel type MRI apparatuses utilizing a horizontal magnetic field have a gantry shape that provides only a narrow space for inserting a subject, and therefore they have a problem that they give a confined feeling to the subject. In order to ameliorate this problem, a part of the gantry around entrance of the imaging bore opened in the front face of the gantry for inserting the subject is formed with a gently curved surface. As a typical shape of the gantry around the entrance part of the bore, there is provided a truncated cone-shaped recessing portion at the circular entrance of the imaging bore to provide a structure that the forwardly protruding frontal outer circumferential surface of the gantry is gently connected to the tunnel-shaped imaging bore via the truncated cone-shaped recessing portion.

PRIOR ART REFERENCES

Patent documents

Patent document 1: Japanese Patent Unexamined Publication (KOKAI) No. 2010-124942
Patent document 2: Japanese Patent Unexamined Publication (KOKAI) No. 2008-5999
Patent document 3: Japanese Design Patent No. 1265497

SUMMARY OF THE INVENTION

Object to be Achieved by the Invention

When imaging of a subject is performed in an MRI apparatus, the subject is laid down on a bed part disposed adjacently to the gantry, the subject is moved into the tunnel serving as an imaging space in that state, and imaging is started. In this case, in order to receive NMR signals from the subject, a receiver coil must be attached to the laying subject. Conventional MRI apparatuses have such problems as explained below concerning workability of the operations for attaching a receiver coil to the subject or resetting the coil.

That is, the bed part is disposed so that one end thereof is in contact with the tunnel-shaped imaging bore of the gantry, and the subject is laid down on a top panel of the bed part, and moved into the inside the tunnel-shaped bore of the gantry together with the top panel. Accordingly, the operator should attach the receiver coil to the subject, or reset it in the vicinity of the entrance of the imaging bore. However, although the truncated cone-shaped recessing portion is provided near the entrance for reducing the confined feeling of the subject, the outer circumference portion of the truncated cone-shaped recessing portion is forwardly protruding, and therefore this protruding portion occupies the motion spaces around the waist and the legs of the operator to force the operator to take an unnatural position. In particular, there is a base for fixing the bed part under the entrance part of the imaging bore, and this base narrows the space for legs of the operator.

Therefore, an object of the present invention is to provide an MRI device that allows favorable access of the operator to the subject at the time of imaging.

Means for Achieving the Object

In order to achieve the aforementioned object, the MRI device of the present invention comprises a gantry containing a static magnetic field generating source for forming a static magnetic field space, and a bed part having a top panel for placing a subject and inserting the subject into the static magnetic field space, and for a front surface of the gantry to which the bed part is connected or fixed, a part of the front surface including a portion around an opening serving as entrance of an open-part (bore) for the static magnetic field space is formed in a recessed shape.

Specifically, the gantry comprises a front panel having an opening serving as entrance of an open-part for the static magnetic field space, and at least a part of the front panel around the opening is formed in a recessed shape. For example, the front panel consists of an arc-shaped outer panel extending from a position above the opening to the ground plane passing the both sides of the opening, and an inner panel disposed inside the arc-shaped outer panel, a portion connecting the outer panel and the inner panel constitutes a forwardly protruding top surface, and the inner panel is formed with a concave curved surface extending from the top surface to the opening.

Alternatively, the front panel comprises a pair of upper front panel and lower front panel disposed upside and downside of the static magnetic field space, and a part of the front panel disposed upside the opening of the static magnetic field space and a part of the front panel disposed downside the opening are formed in a recessed shape recessing from portions thereof connected to the front panels.

Effect of the Invention

According to the present invention, a recessed hollow is formed in the front surface of the gantry around the opening up to the ground plane, and this hollow can be used for access of an operator to a subject at the time of imaging.

BRIEF DESCRIPTION OF THE DRAWINGS

FIG. 1, (a) is a schematic outer view, and (b) is a partial top view.

FIG. 8, (a) shows a state before the connection, (b) shows a state after the connection, and (c) is a horizontal cross-sectional view.

FIG. 9, (a) shows a state that the top panel has ascended, and (b) shows a state that the top panel has descended.

FIG. 10, (a) is a side view, (b) is a top view, and (c) shows a motion space of the operator.

FIG. 11, (a) is a schematic outer view, and (b) is a cross-sectional view of the body of the device.

MODES FOR CARRYING OUT THE INVENTION

EXAMPLE 1

Hereafter, one example of the MRI device of the present invention will be explained with reference to FIGS. 1 to 10. In all the drawings, the same numerals are attached to the parts having the same functions, and repetitive explanations are omitted.

Figure 1:
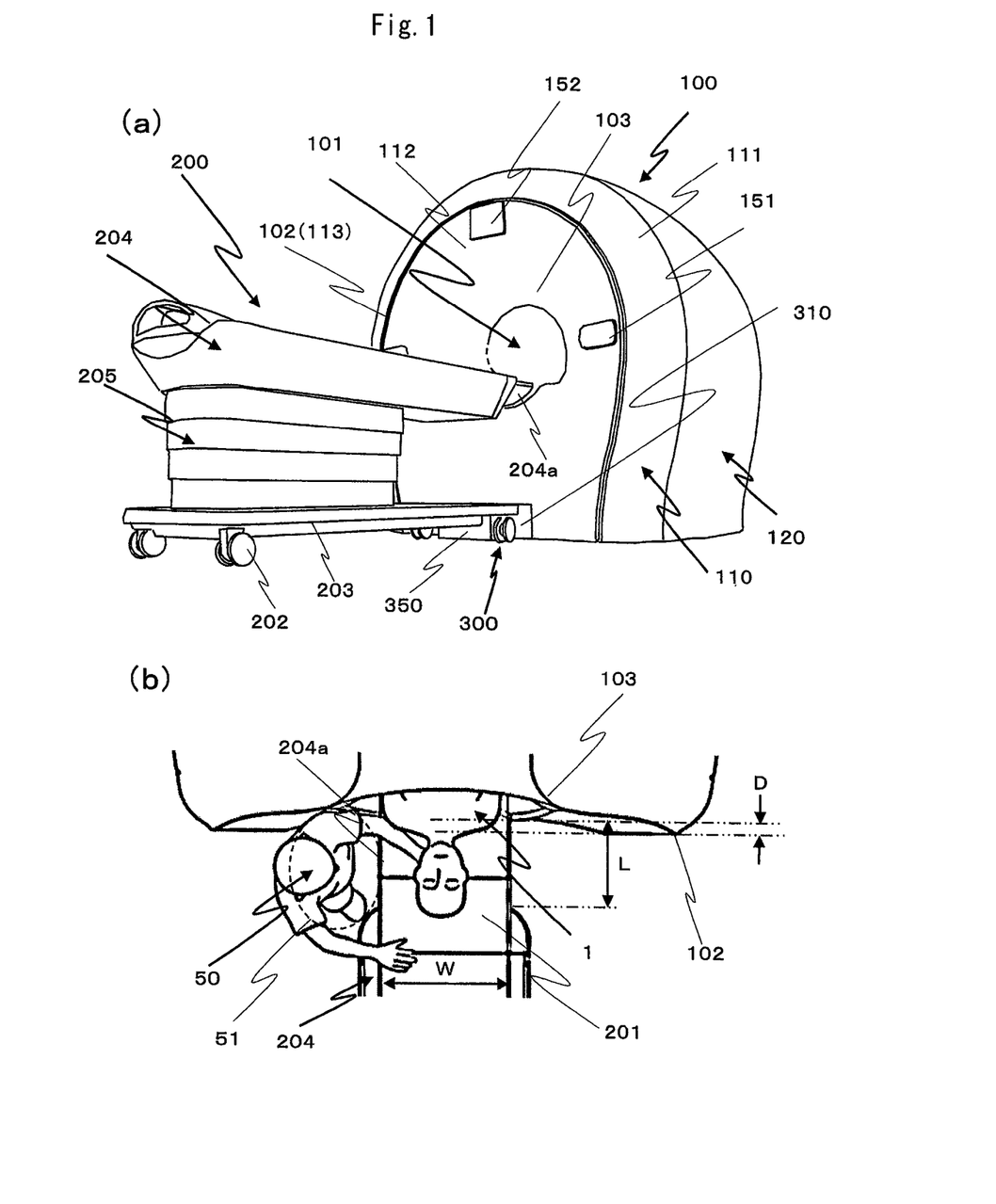
FIG. 1 includes drawings showing an example of the MRI device of the present invention.

First, with reference to FIG. 1, the outline structure of the MRI device of this example will be explained. FIG. 1, (a) shows a schematic structure of a gantry 100 and a bed part 200 of the MRI device according to the present invention, and (b) is a partial top view of the MRI device, which shows an operator 50 who accesses a subject 1. The MRI device of this example has a horizontal magnetic field type structure for generating a static magnetic field in the direction parallel to the body axis direction of the subject 1 laid on the bed.

This MRI device shown in FIG. 1 comprises the gantry 100 accommodating various apparatuses for inducing NMR in the subject 1 and receiving NMR signals, the bed part 200 having a top panel 201 for placing the subject 1, a control housing not shown in the drawing accommodating power supplies for driving the various devices in the gantry 100 and various control units for controlling the devices, and a processing unit for processing received NMR signals to reconstruct a tomographic image of the subject, and they are connected with power supplies and signal wires not shown in the drawing. At the front (on the front surface) of the gantry 100, an operation panel 151 for operating the control units and the processing unit, and a status display part 152 for displaying states of devices, patient, and so forth.

The gantry 100 and the bed part 200 are disposed in a shield room not shown in the drawing for shielding radio frequency electromagnetic waves and static magnetic field, and the control housing and the processing unit are disposed out of the shield room. Therefore, operations of the operator 50 for controlling irradiation intensity, moving the top panel 201, etc. and confirmation thereof are performed through the operation panels 151 disposed in front of the gantry 100 and on the right and left sides of a bore (open-part) 101 and the status display part 152 disposed in front of the gantry 100 and on the upside of the bore 101.

In this MRI device, the tunnel-shaped bore 101 is provided substantially at the center of the gantry 100, so that the subject 1 in a state of being laid on the top panel 201 of the bed part is inserted into a static magnetic field space in this bore 101.

Further, in this example, the bed part 200 comprises free wheels 202, and it is a movable bed part that can move in a state that the subject 1 is placed on the top panel 201. Therefore, a connection part 300 for connecting and fixing the bed part 200 to the gantry 100 is provided in this MRI device. The connection part 300 consists of a gantry-side connection part 310 and a bed-side connection part 350. According to this example, for example, the subject 1 placed on the bed part 200 outside the shield room can be moved into the shield room together with the bed part 200, the bed part 200 can be connected and fixed to a predetermined position of the gantry 100, and then imaging can be performed.

Further, in this example, a support apparatus that draws the top panel 201 of the bed part 200 into the bore 101 and supports the top panel 201 can be attached on the side of the gantry 100 opposite to the side on which the bed part 200 is connected.

One of the important features of the MRI device of this example is that a recessed entrance part 103 of the bore is provided around the entrance of the bore 101, which entrance part 103 connects the forwardly protruding top surface 102 and the tunnel-shaped bore 101 with a gently curved surface that gradually retreats from the top surface 102, and the recessed entrance part 103 of the bore formed at a position retreated from top surface 102 is formed so as to extend to a frontal lower part of the gantry 100.

That is, in the conventional MRI devices, in order to ameliorate the confined feeling given to the subject 1 by the tunnel-shaped bore 101, of which entrance is formed at the front of the gantry 101, the entrance part of the bore 101 has a largely curved shape formed by cutting out a portion around the entrance. That is, in the conventional apparatuses, around the entrance of the tunnel-shaped bore 101, a convexly protruding peripheral part is formed. Therefore, when the bed part 200 is connected to the bore 101, it is difficult to secure a space for the operator 50 to perform the operations of attaching a receiver coil to the subject 1, or resetting it in the vicinity of the bore 101.

In particular, it is difficult to secure sufficient spaces for the operator 50 on the both sides of the top panel 201 or under the top panel 201, because the convexly protruding periphery or the connection part for connection with the bed part 200 obstructs the operator, although a working space for the operator may be secured to a certain extent above the top panel since there is the bore 101, or a portion around the entrance of the bore 101 is cut out.

Therefore, in this example, the conventional shape that the forwardly protruding top surface 102 formed around the entrance of the bore 101 goes around the bore 101 up to a position corresponding to the lower part of the bore 101 is not employed, but there is employed a shape that the top surface 102 extends downward on the both sides of the bore 101. Specifically, the front panel 110 constituting the front surface of the gantry 100 is constituted with an arc-shaped outer panel 111 connected to a circumferential panel 120 of the gantry 100 and an inner panel 112 attached to the arch-shaped outer panel 111, the connection part of these outer panel 111 and inner panel 112 is formed as the most forwardly protruding top surface 102, and the inner panel 112 is formed with a gently curved surface retreating from the panel connection part 113 (top surface 102) to secure a working space for the operator.

The inner panel and the outer panel need not be necessarily constituted with separate members, and they may be formed as one body.

Another important feature of the MRI device of this example is that a top panel base part 204 for supporting the end of the top panel 201 is provided so that the top panel 201 can protrude from the end of the bed part 200 along the longitudinal direction on the side to be connected to the gantry 100, and an end part 204a of the top panel base part 204 has a width not larger than the width of the top panel 201.

That is, in the conventional bed part 200, the top panel base part 204 is provided above a base housing 203 via a lift 205, and the top panel 201 is provided on this top panel base part 204. Because this top panel 201 is slid along the longitudinal direction of the top panel base part 204, there is employed a structure that the top panel base part 204 has a width larger than that of the top panel 201, and when the top panel 201 is retracted, the top panel 201 is stored within the top panel base part 204.

However, in such a conventional structure, when the bed part 200 is connected to the gantry 100, the top panel base part 204 having a width larger than that of the top panel 201 approaches the gantry 100, therefore it becomes difficult to secure a working space for the operator, and the operator is forced to take an unnatural position.

Therefore, in this example, as shown in FIG. 1, (b), the end part 204a of the top panel base part 204 on the side of the gantry 100 is formed so as to have the same width as the width W of the top panel 201, or exist within the projected area of the top panel 201. Therefore, in this example, the bed part 200 and the gantry 100 are connected so that the end of the top panel 201 protrudes in a length of L along the longitudinal direction from the end of the top panel base part 204 having a larger width. Accordingly, when they are connected, the portion of the top panel base part 204 around the top panel 201 connected to the gantry 100 has the minimum width W of the top panel 201 for holding the subject 1, and therefore working spaces 51 for the operator 50 can be secured on both sides of the top panel 201. In addition, the top panel 201 is supported at both sides by the top panel base part 204 except for the end portion of the top panel 201 (length: L), the subject 1 laid on the top panel 201 can be supported without giving a feeling of uneasiness (unstableness) to the subject 1.

Further, a further important feature of the MRI device of this example is that the gantry-side connection part 310 is formed at a position retreated from the panel connection part 113 in the inner panel 112 existing within the projected area of the top panel 201.

That is, in a state that the bed part 200 and the gantry 100 are connected, when the operator 50 accesses the subject 1 in the vicinity of the entrance part 103 of the bore, if a space cannot be secured around the legs of the operator 50, the operator is forced to perform the operation at an unnatural position. In this example, in order to solve this problem, the gantry 100 is designed to have a frontal lower part thereof right below the entrance part 103 of the bore at a position retreated from the top surfaces 102 of both sides by a depth D, the gantry-side connection part 310 is formed at this retreated position, and in addition, it is provided within the projected area of the top panel 201 connected to the gantry 100. Working spaces 51 for the operator 50 can be thereby secured on both sides of the gantry-side connection part 310.

Although the aforementioned example uses the so-called dockable table that enables connection of the bed part 200 and the gantry 100, the present invention is not limited to such a type of apparatus, but can of course be also applied to an MRI apparatus using a fixed bed.

Figure 2:
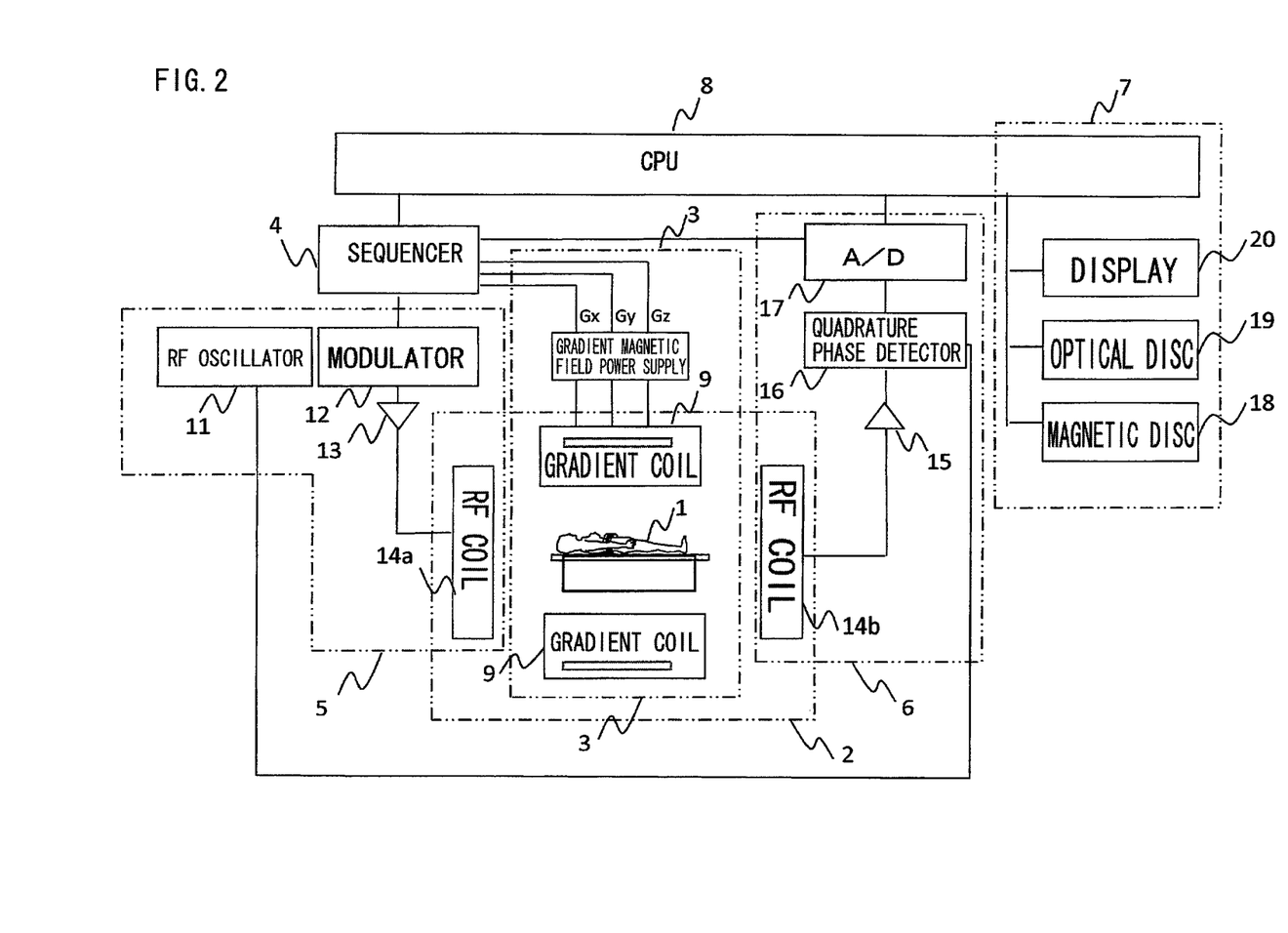
FIG. 2 is a block diagram of the MRI device of the present invention.
Figure 3:
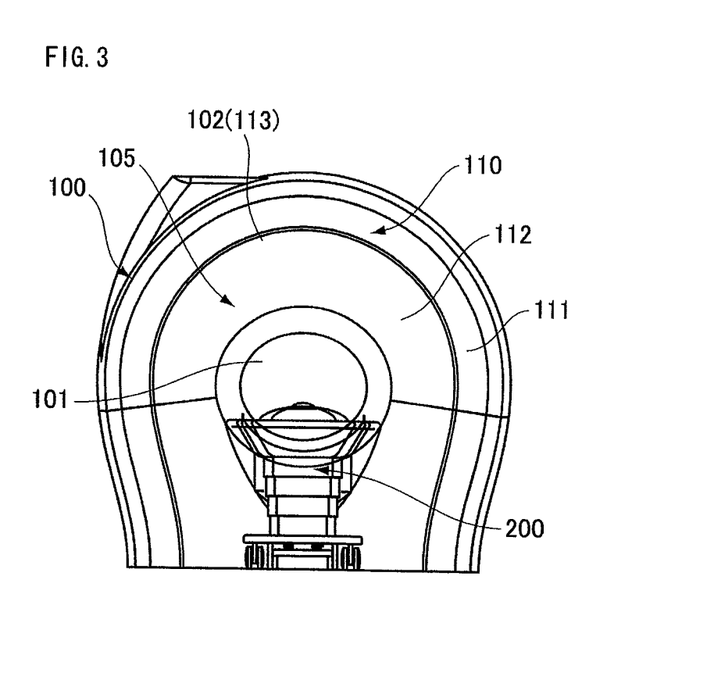
FIG. 3 is a front view of the gantry and the bed part of the MRI device of the present invention.
Figure 4:
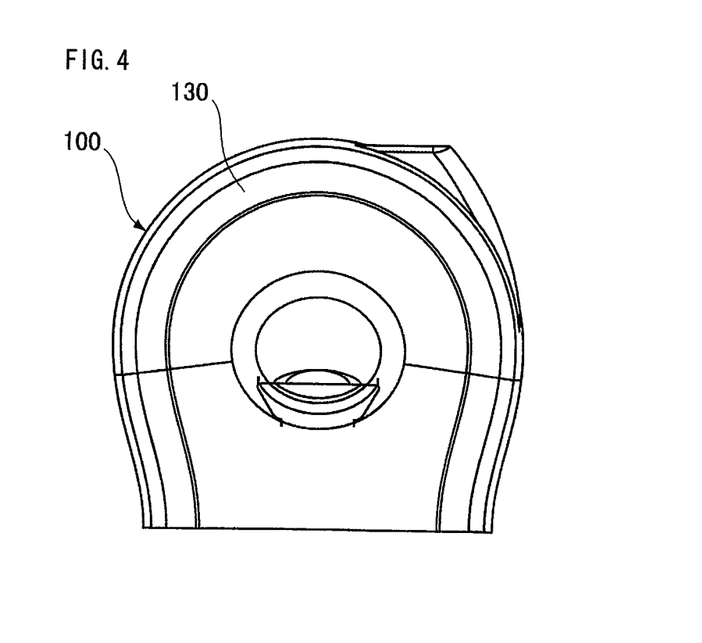
FIG. 4 is a back view of the gantry and the bed part of the MRI device of the present invention.
Figure 5:
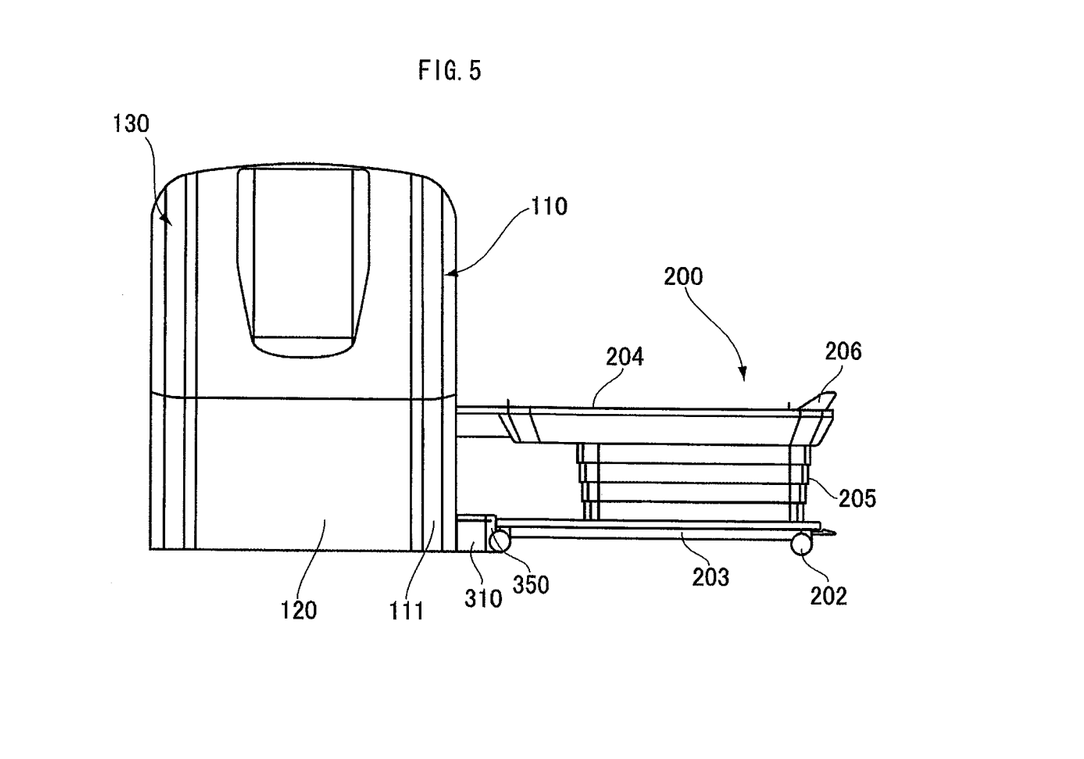
FIG. 5 is a left side view of the gantry and the bed part of the MRI device of the present invention.
Figure 6:
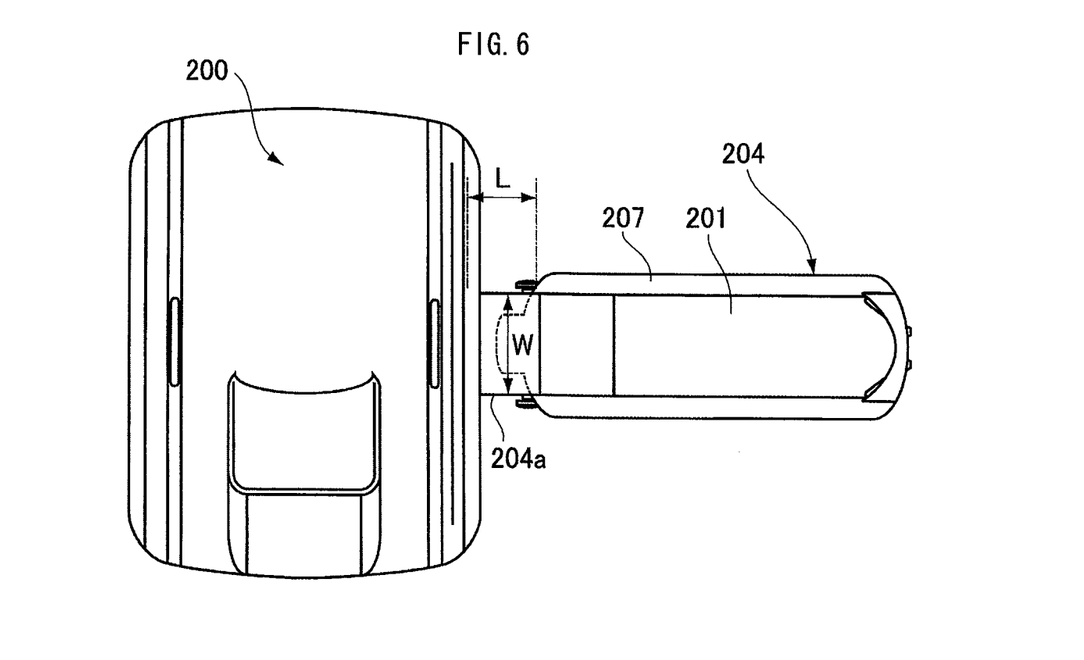
FIG. 6 is a plane view of the gantry and the bed part of the MRI device of the present invention.
Figure 7:
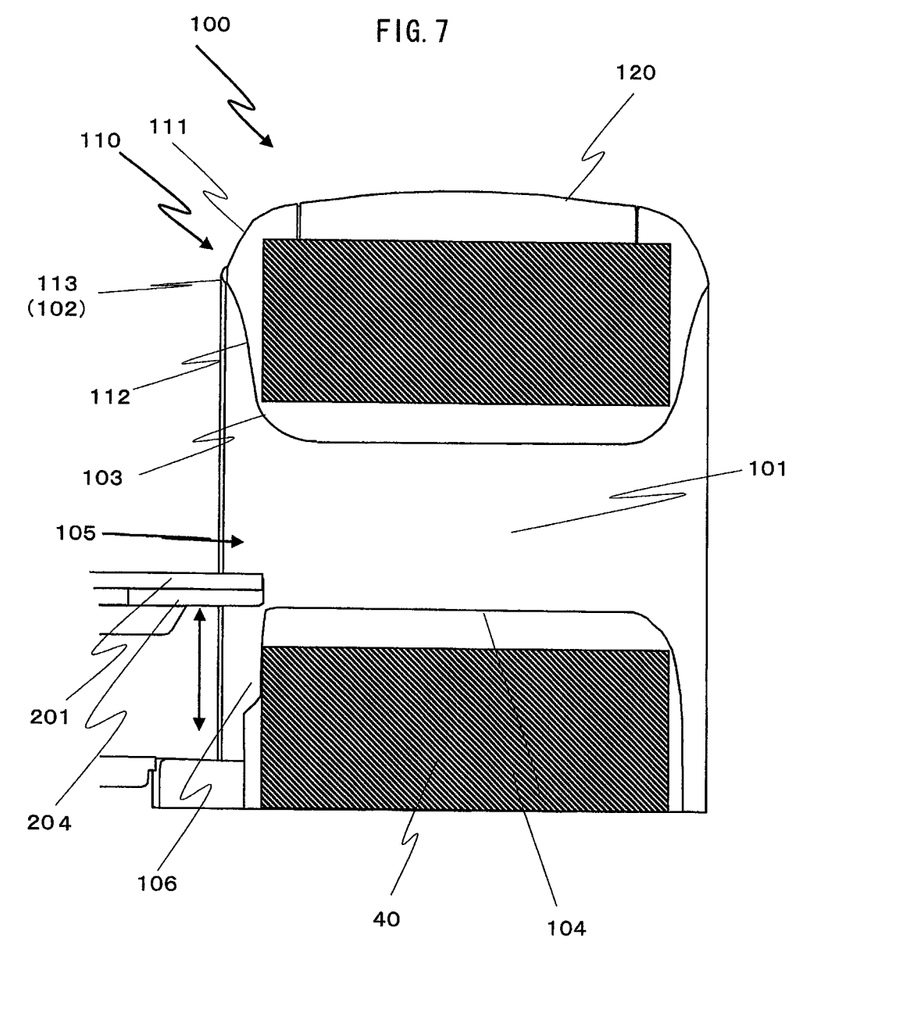
FIG. 7 is a cross-sectional view at an essential position of the gantry and the bed part of the MRI device of the present invention.
Figure 8:
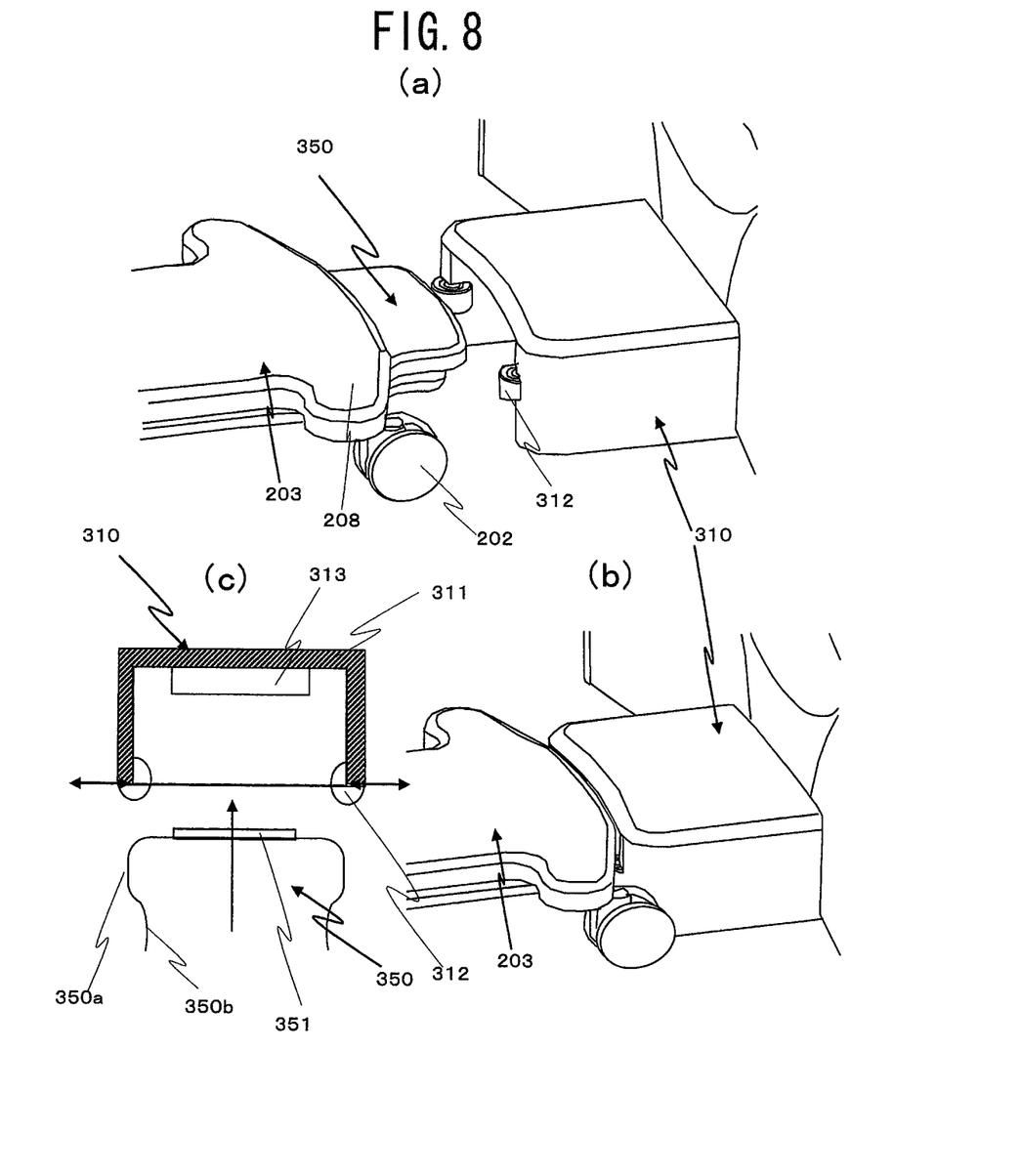
FIG. 8 includes drawings for explanation of parts for connection of the gantry and the bed part.
Figure 9:
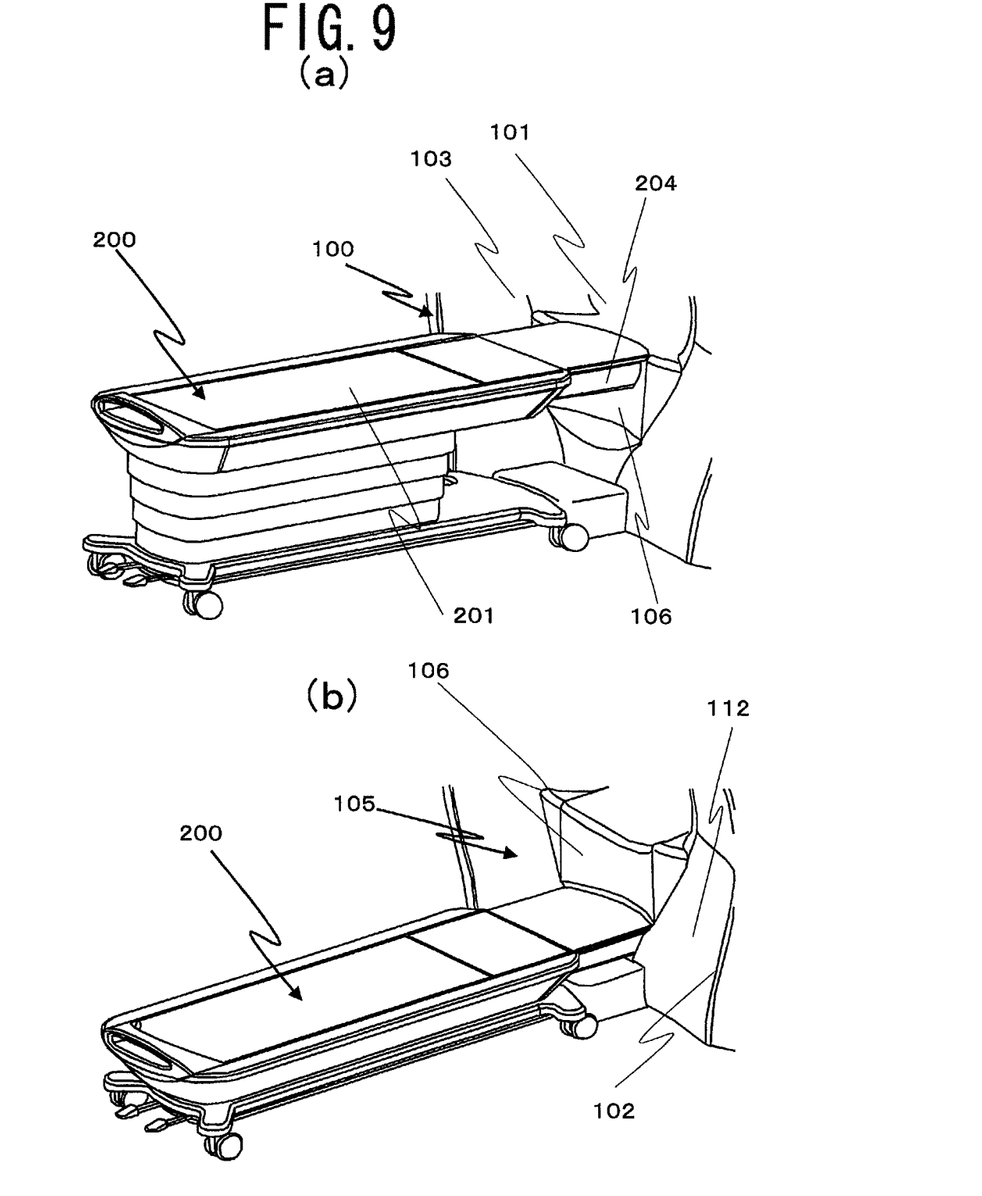
FIG. 9 includes drawings for explanation of connection state of the gantry and the bed part.
Figure 10:
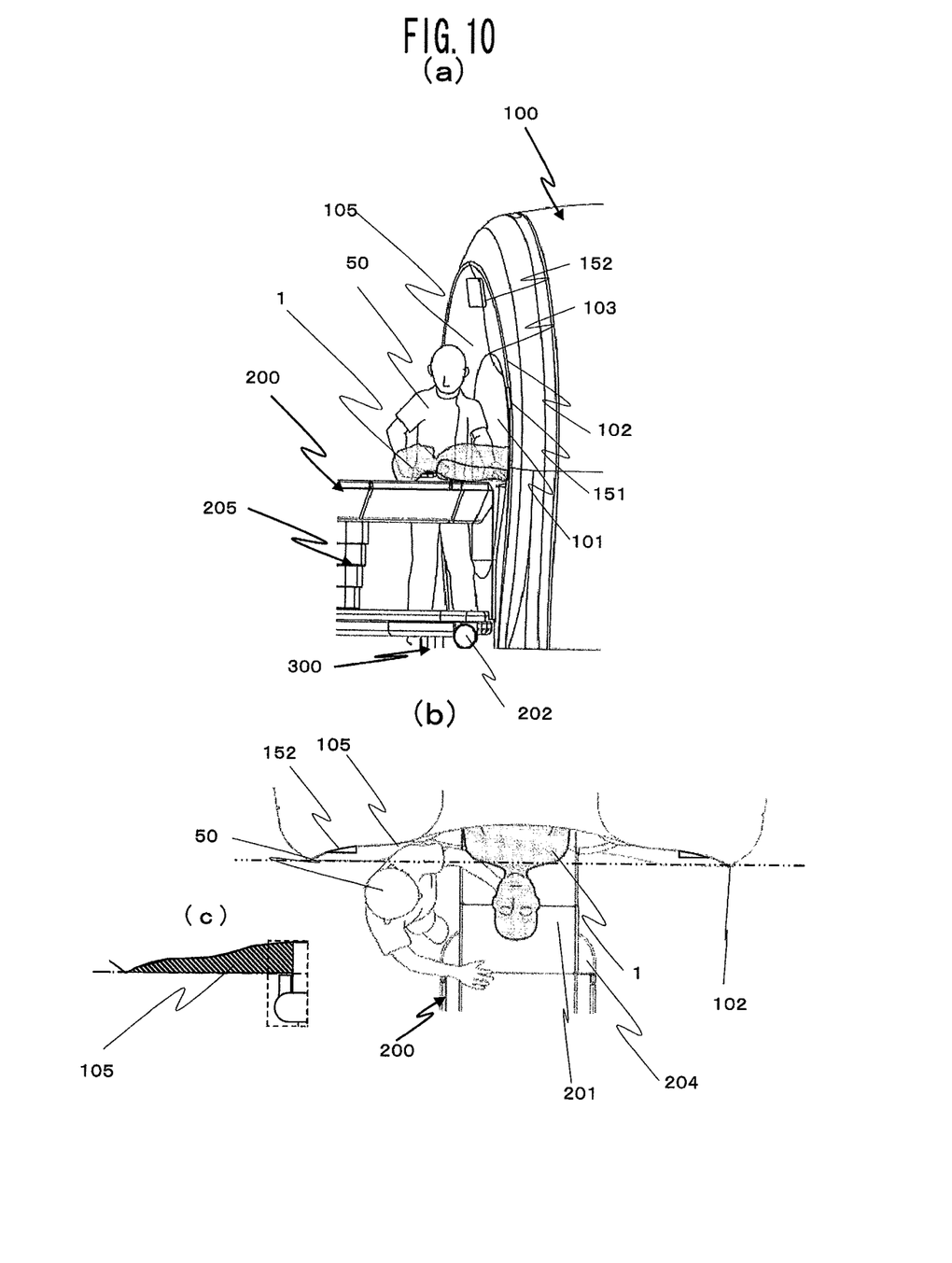
FIG. 10 includes drawings for explanation of states of the MRI device of the present invention in use.

Hereafter, the MRI device of this example will be explained in more detail with reference to FIGS. 2 to 10. FIG. 2 is a block diagram of the MRI device according to the present invention. FIGS. 3 to 6 are external views of the gantry and the bed part of the MRI device. FIG. 3 is a front view, FIG. 4 is a back view, FIG. 5 is a left side view, FIG. 6 is a top view, and FIG. 7 is a cross-sectional view of an essential part. FIG. 8 includes explanatory views for the connection part of the gantry and the bed part. FIG. 9 includes explanatory views showing the connection state of the gantry and the bed part. FIG. 10 includes explanatory views showing the apparatus in use.

First, with reference to FIG. 2, the configuration of the MRI device will be explained in more detail for every specific function. As shown in FIG. 2, the MRI device comprises a static magnetic field generating system 2, a gradient magnetic field generating system 3, a transmitting system 5, a receiving system 6, a signal-processing system 7, a sequencer 4, and a central processing unit (CPU) 8.

The static magnetic field generating system 2 generates a uniform static magnetic field in a space surrounding the subject 1 in the body axis direction (horizontal magnetic field method), and consists of a normal conduction or superconduction type static magnetic field generation source disposed around the subject 1. The static magnetic field generating system 2 is accommodated in the gantry 100 shown in FIG. 1.

The gradient magnetic field generating system 3 consists of gradient coils 9 that generate gradient magnetic fields in three-axis directions of X, Y, and Z, and gradient magnetic field power supplies 10 for driving the gradient coils 9, and the gradient magnetic field power supplies 10 for the coils are driven according to commands sent from the sequencer 4 described below to irradiate gradient magnetic fields Gx, Gy, and Gz for the three-axis directions of X, Y, and Z on the subject 1. For example, a slice direction gradient magnetic field pulse (Gs) is applied along one of the directions of X, Y, or Z to determine a slice plane of the subject 1, and a phase encoding direction gradient magnetic field pulse (Gp) and a frequency encoding direction gradient magnetic field pulse (Gf) are applied along the remaining two directions to encode positional information for the directions in echo signals. The gradient coils 9 are accommodated in the gantry 100 shown in FIG. 1, and the gradient magnetic field power supplies 10 are accommodated in the control housing not shown in the drawing.

The sequencer 4 is a control means for repeatedly applying a radio frequency magnetic field pulse (henceforth referred to as RF pulse), and a gradient magnetic field pulse in the form of a certain predetermined pulse sequence, and it operates according to control by the CPU 8 and send various commands required for collection of data for tomographic images of the subject 1 to the transmitting system 5, the gradient magnetic field generating system 3, and the receiving system 6. The sequencer 4 is accommodated in the control housing.

The transmitting system 5 irradiates an RF pulse in order to induce nuclear magnetic resonance in nuclear spins of atoms constituting biological tissues of the subject 1, and comprises a radio frequency oscillator 11, a modulator 12, a radio frequency amplifier 13, and a transmitting radio frequency coil 14a. A radio frequency pulse outputted from the radio frequency oscillator 11 is amplitude-modulated with the modulator 12 at a timing sent by the sequencer 4, and this amplitude-modulated radio frequency pulse is amplified with the radio frequency amplifier 13 and supplied to the radio frequency coil 14a disposed in the vicinity of the subject 1 to irradiate an RF pulse on the subject 1. In general, the radio frequency coil 14a is accommodated in the gantry 100, and the other components are accommodated in the control housing.

The receiving system 6 detects echo signals (NMR signals) emitted by the nuclear magnetic resonance of the nuclear spins of atoms constituting biological tissues of the subject 1, and comprises a receiving radio frequency coil 14b, a signal amplifier 15, a quadrature phase detector 16, and an A/D converter 17. Responsive NMR signals emitted from the subject 1 induced by the electromagnetic waves irradiated from the transmitting radio frequency coil 14a are detected with the radio frequency coil 14b disposed in the vicinity of the subject 1, amplified by the signal amplifier 15, and then divided into two orthogonal signals by the quadrature phase detector 16 at a timing sent from the sequencer 4, and each signal is converted into digital quantity by the A/D converter 17, and sent to the signal-processing system 7. The devices constituting the receiving system 6 are generally accommodated in the gantry 100.

The signal-processing system 7 comprises an external storage device consisting of an optical disc 19, a magnetic disc 18 or the like, and a display 20 consisting of a CRT or the like, and when data sent from the receiving system 6 are inputted into CPU 8, CPU 8 performs operations of signal processing, image reconstruction, and so forth, displays the result of the operations, i.e., a tomographic image of the subject, on the display 20, and records it on the magnetic disc 18 etc. of the external storage device. The signal-processing system 7 is accommodated in the processing unit. The transmitting radio frequency coil 14 and the gradient coils 9 are disposed in the static magnetic field space of the static magnetic field generating system 2 into which the subject 1 is inserted, so as to face the subject 1. Further, the receiving radio frequency coil 14b is disposed so as to face or surround the subject 1.

The presently widely used nuclide for clinical imaging by MRI apparatuses is hydrogen nucleus (proton), which is a main constitutional substance of the subject. By imaging information about spatial distribution of proton density, or spatial distribution of relaxation time of excited state, morphology or function of human head, abdominal part, extremities and so forth are two-dimensionally or three-dimensionally imaged.

Hereafter, specific structures of the gantry 100 and the bed part 200 will be further explained with reference to FIGS. 3 to 7.

The gantry 100 is explained first. The gantry 100 of this example has a basic shape for securing horizontal plane (ground plane) in order to secure stability of the lower part of the laid cylindrical shape with respect to the floor. As for the front shape shown in FIG. 3 and the back shape shown in FIG. 4, it has a circular shape for the upper part, and the width of the lower part is slightly narrowed for the both sides, but it becomes larger at the lower end. As for the side shape shown in FIG. 5, the center part is covered with a circumferential panel 120, and both sides thereof are constituted with a front panel 110 and a back panel 130 of the same shape.

In the gantry 100, a magnet 40 shown as one component is disposed so as to surround the tunnel-shaped bore 101 as shown in FIG. 7, the external surface of this magnet 40 is covered with the circumferential panel 120, and the internal surface of the magnet 40 is covered with a cylindrical member 104.

The front panel 110 constituting the anterior part of the gantry 100 consists of the outer panel 111 connected to the circumferential panel 120, and the inner panel 112 constituting an inside part of the outer panel 111, as shown in FIG. 3. Since the back panel 130 has the same shape as that of the front panel 110, the explanation thereof is omitted.

The outer panel 111 of the front panel 110 is formed with a convex curved surface of which width is forwardly narrowed, and the panel connection part 113 as the front end of the outer panel 111 constitutes the top surface 102 of the front panel 110. In this example, this panel connection part 113 is formed with a thin sash-shaped belt-like member. The outer panel 111 and the inner panel 112 of the front panel may not be constituted with separate members, but they may be formed as one member, and in such a case, the most forwardly protruding line-shaped or belt-shaped portion constitutes the top surface.

The whole inner panel 112 is constituted with a concave curved surface, which significantly recesses in the vicinity of the top surface 102 as the outer circumference thereof and is smoothly connected to the entrance part 103 of the bore 101 formed with a convex curved surface in the vicinity of the bore 101. In the conventional structure, the housing surrounding the magnet 40 is generally formed with a roundly convex curved surface, but the inner panel 112 of this example is formed with a concave curved surface contrary to the conventional structure, and thereby a recessed part 105 is formed with the concave curved surface in the anterior part of the gantry 100. In particular, one of the features of this example is that the panel connection part 113 is extended downward for both ends thereof to extend the recessed part 105 up to the ground plane as shown in FIGS. 3 and 4, not using a structure that the panel connection part 113 constituting the top surface 102 is rounded up to a position corresponding to the lower part of the bore 101 to surround the recessed part 105 with the panel connection part 113. According to this structure, a part of the space formed by recession of the recessed part 105 can be used as the working space 51 for the operator 50.

The inner panel 112 and the cylindrical member 104 may be formed with light-transmitting milky white resin members. In such a case, an LED light source not shown in the drawing can be provided at a certain position of the inside to emit light from the inner panel 112 and the cylindrical member 104 and thereby realize illumination exhibiting decorative stage effects, and therefore a feeling of uneasiness of the subject 1 can be reduced.

As shown in FIGS. 5 and 7, the thin box-shaped gantry-side connection part 310 is provided at the center of the lower end of the recessed part 105 of the inner panel 112. This secures a space for connection with the bed-side connection part 350, and also makes the protruding length of the gantry-side connection part 310 protruding from the front surface of the gantry 100 smaller. In particular, since the bed part 200 can be moved in this example, it is effective to make the protruding length of the gantry-side connection part 310 exposed at the time of this movement smaller.

Although the circumference of the entrance part 103 of the bore is formed with the recessed shape in this example, the recession may not necessarily be provided all the circumference of the entrance part. This is because even if only a lower part or a left or right side part of the entrance part is recessed, access of the operator is made easier, and feeling of openness can be created. In such a case, a light source such as laser, display, etc. may of course be provided at the upper part of the entrance part.

Hereafter, the details of the bed part 200 will be explained with reference to FIGS. 5 and 6.

The bed part 200 comprises the base housing 203 having the free wheels 202 at the four corners, the top panel base part 204 provided with the slidable top panel 201, and the bellows lift 205 connecting the top panel base part 204 and the base housing 203. As shown in FIG. 5, in this example, the top panel base part 204 is faced the base housing 203 from above, and the lift 205 is provided between them at a position shifted toward one side along the longitudinal direction. There is thereby provided a structure that, at the end of the other side for the longitudinal direction, the middle part is opened, and the upper top panel base part 204 and the lower base housing 203 protrude.

In this example, the bed-side connection part 350 is provided on the base housing 203 protruding to the other end side, and the end part 204a of the top panel base part 204 protruding to the other end side is formed in the same width W as that of the top panel 201. Further, a handle 206 used for moving the top panel 201 or moving the bed part 200 itself is provided on one end side of the top panel 201 above the lift 205. Of course, this handle 206 may be constituted with a handle for sliding the top panel 201, and a handle for moving the bed part 200 itself, and they may be separately provided at similar positions.

According to this structure of the bed part 200, the lift 205 is disposed at a position shifted toward one end along the longitudinal direction to provide the center of gravity of the bed part 200 at a position shifted toward that end side along the longitudinal direction, and the handle 206 is disposed on the side of the one end toward which the position of the center of gravity is shifted to make mobility with the free wheels 202 favorable. In addition, by disposing the lift 205 at a position shifted toward one end, a wide working space can be secured on the side of the other end along the longitudinal direction, in which the operator is not obstructed by the lift 205, and therefore workability of the operator can be made favorable.

Further, as shown in FIG. 6, supporting surfaces 207 forming a smooth continuous surface together with the upper surface of the top panel 201 are provided on the both sides of the top panel base part 204 of this example for the transverse direction except for the parts of the end part 204a of the top panel base part 204 having the same width as that of the top panel 201. According to this structure, in a state that the top panel 201 is retracted on the top panel base part 204, a wide smooth surface is formed by most of the top panel 201 and the supporting surfaces 207 on the both sides thereof, and therefore even if the bed part 200 is moved, the subject 1 can be stably supported with the top panel 201 and the supporting surfaces 207. At the time of imaging, only the narrow top panel 201 on which the subject 1 is placed can be inserted into the tunnel-shaped bore 101.

Furthermore, if the bed part 200 is connected to the gantry 100 via the connection part 300, the end part 204a of the top panel base part 204 in the vicinity of the gantry 100 is contained within the width W the same as that of the narrow top panel 201. In addition, the end part 204a of this top panel base part 204 is inserted into the recessed part 105 formed in the front of the gantry 100, and therefore the space of the recessed part 105 and space in the vicinity of the end part 204a can be used as a working space for the operator.

Hereafter, the structure of the connection part 300, and the connecting state of the gantry 100 and the bed part 200 when they are connected will be further explained with reference to FIGS. 7 to 9.

First, as shown in FIG. 8, wheel supporting parts 208 for supporting the free wheels 202 are formed at one end of the base housing 203 of the bed part 200 so as to protrude on both sides along the transverse direction of the base housing 203. That is, in this example, the wheel supporting parts 208 are protrudingly formed at the four corners of the base housing 203, and stable movement can be realized by the free wheels 202 supported by these wheel supporting parts 208.

Further, as shown in FIG. 8, (a), between one pair of the wheel supporting parts 208 on the side of one end of the base housing 203 along the longitudinal direction, there is formed the bed-side connection part 350 protruding on the side of the one end. As shown in FIG. 8, (c), this bed-side connection part 350 has such a shape that the both sides 350a of the tip part protrude outward, and inside parts 350b of the tip part recess inward. Further, a female connector 351 that electrically connects the bed part 200 with the gantry 100 is provided at the tip thereof.

On the other hand, the gantry-side connection part 310 is provided with a box-shaped connection housing 311 for accommodating the bed-side connection part 350. Spring members 312 for absorbing stress to both sides are provided on the both sides of the tip part of this connection housing 311, and a male connector 313 for connection with the female connector 351 is provided inside the connection housing 311 (FIG. 8, (c)).

According to this example, when the bed-side connection part 350 in a state shown in FIG. 8, (a) is inserted into the connection housing 311 of the gantry-side connection part 310, entry of the both sides 350a of the tip part of the bed-side connection part 350 is prevented by the spring members 312 at first, but the spring members 312 absorb the stress at that time, and therefore the bed-side connection part 350 can be inserted into the connection housing 311 to realize the state shown in FIG. 8, (b). Further, in this inserted state, connection of the female connector 351 and the male connector 313 can be attained, the spring members 312 fit with the insides 350b of the recessed tip part, and therefore the gantry-side connection part 310 and the bed-side connection part 350 are fixed. In addition, since the width of the connection housing 311 is designed to be smaller than the distance between the free wheels 202 of the both sides, a pair of the free wheels 202 can be retracted on both sides of the gantry-side connection part 310 as shown in FIG. 8, (b), and therefore obstruction by the free wheels 202 can be reduced.

Hereafter, ascend and descend of the bed part 200 will be explained. In the bed part 200 of this example, the top panel 201 can ascend and descend by means of the lift 205 as described above. In addition, the bed part 200 has such a structure that enables ascent and descent of the top panel 201 even in a state that the bed part 200 is connected to the gantry 100. For this purpose, as shown in FIGS. 9 and 7, a recessed orbital part 106 that secures an ascending and descending orbit for the top panel 201 and the top panel base part 204 supporting it is continuously formed in the gantry 100 at a position under the entrance part 103 of the bore.

That is, as shown in FIG. 7, in a state that the bed part 200 and the gantry 100 are connected, the tip of the top panel 201 is set at a height enabling insert thereof into the bore 101. Then, in this setting state, the tips of the top panel 201 and the top panel base part 204 supporting the top panel are at a position within the inside of the entrance part 103 at a lower part thereof. A recess (recessed orbital part 106) continuously extending downward for receiving the tips of the top panel 201 and the top panel base part 204 is provided under the lower end of the entrance part 103 of the bore, and this recess is used as the recessed orbital part 106 that enables ascent and descent of the top panel 201.

According to this example, as shown in FIG. 9, (a), even in a state that the bed part 200 is connected with the gantry 100, the top panel 101 can descend to the state shown in FIG. 9, (b). The contrary is also possible. Since the top panel 101 can ascend or descend even in the connected state as described above, the subject 1 can easily get on and off the top panel 101. Further, according to this example, the recessed inner panel 112 provided from the top surface 102 toward the inside and the recessed orbital part 106 can be continuously formed to form a recessed part 105 serving as a further larger recess, and a wider space can be thereby secured around the legs of the operator.

Hereafter, workability of the operator 50 with this MRI device will be further explained with reference to FIG. 10. As shown in FIG. 10, the front face of the gantry 100 has the top surface 102 continuously extending on the upper part and the both side parts thereof, and the recessed part 105 is formed from this the top surface 102 to the entrance part 103 of the bore in the vicinity of the bore 101 with a concave curved surface. Therefore, the operator 50 can access the subject 1 laid on the bed part 200, with inserting the shoulder and the waist into the recessed part 105. In addition, the operator 50 can perform the operation through the operation panel 151, or confirm the state through the status display part 152, both provided in the recessed part 105, at the time of the access.

Further, since the recessed inner panel 112 formed inward from the top surface 102 and the recessed orbital part 106 (refer to FIG. 9) can be continuously provided as shown in FIG. 10, (c) to form the recessed part 105 serving as a further larger recess as described above, a wide space can be secured around the legs of the operator. Furthermore, since the width of the top panel base part 204 is set to be not larger than the width of the top panel 201 for the portion near the recessed part 105, the top panel base part 204 does not obstruct the operator 50 who supports the subject. Moreover, since the lift 205 that supports the top panel base part 204 is provided at a position shifted toward one side, there is secured a wide space around the legs of the operator (space for movements of the legs of the operator 50) under the top panel 201 in the vicinity of the recessed part 105. Therefore, hitting of the knees of the operator 50 against the lift 205 can be prevented, the operator 50 can also insert the legs into the space under the top panel 201, and thus workability of the operator 50 can be markedly improved.

Since the connection part 300 is provided at a position near the ground plane within the projected area of the top panel 201, the space around the legs of the operator 50 can be secured wider, when the operator 50 is at a position for supporting the subject 1. In addition, since the free wheels 202 are retracted on the both sides of the connection part 300, the free wheels 202 can be prevented from obstructing the operator 50.

As explained above, the MRI device according to this example comprises the gantry containing the static magnetic field generating source for forming a static magnetic field space, and the bed part having the top panel for placing the subject and inserting the subject into the static magnetic field space, the gantry is provided with the outer circumferential panel covering the outer circumference of the tunnel-shaped static magnetic field space, and the front panel having the opening serving as entrance of the bore for the static magnetic field space, and at least a part of the front panel in the vicinity of the opening is formed in a recessed shape.

In the MRI device of this embodiment, the front panel of the gantry may comprise an arc-shaped outer panel extending from the upper part of the opening to the ground plane via both sides of the opening, and an inner panel disposed inside the outer panel, a portion connecting the outer panel and the inner panel may constitute a top surface protruding forwardly, and the inner panel may be formed in a recessed shape with a concave curved surface extending from the top surface to the opening.

The bed part is provided with the top panel base part on which the slidably movable top panel is provided, and this top panel base part is formed with a width of the end to be connected to the gantry not larger than the width of the top panel. Further, the bed part has the connection part that enables attachment and detachment of the bed part to or from the gantry, the connection part is constituted with the gantry-side connection part provided at the center of the lower part of the inner panel retreated from the top surface of the gantry, and the bed-side connection part provided at one end side of the bed part for the longitudinal direction, and the bed-side connection part is provided at the end of the base housing having four wheels for transfer. Furthermore, the bed part is provided with the base housing having wheels for transfer at the four corners and the lift on the base housing, which supports the top panel base part having the slidably movable top panel and enables ascent and descent of the top panel base part, and a recess extending downward from a position corresponding to the lower end of the opening is formed in the inner panel, so that the top panel base part can ascend and descend by means of the lift along this recess.

EXAMPLE 2

Although a so-called tunnel type MRI device was mainly explained in the aforementioned example, an example of so-called open type MRI device to which the present invention is applied will be explained in this example. The same numerals are attached to the parts having the same functions, and repetitive explanations are omitted.

Figure 11:
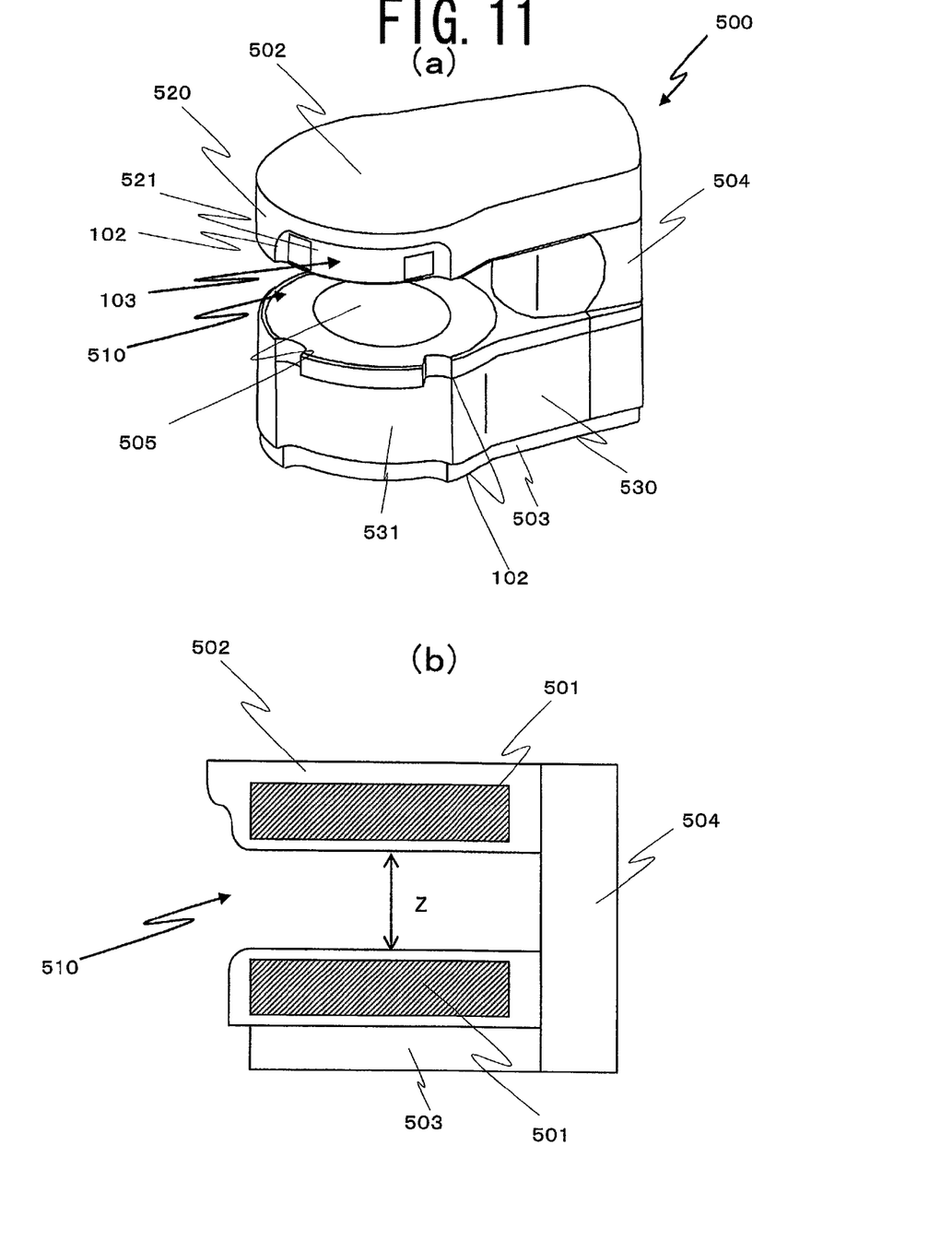
FIG. 11 includes drawings showing another example of the MRI device of the present invention.

An exemplary configuration of open type MRI device is shown in FIG. 11, (a), a sectional view of the main part of the apparatus is shown in FIG. 11, (b), and explanation will be made below with reference to these drawings.

The MRI device 500 of this example comprises the main part of the MRI device 500 having a pair of magnets 501 disposed on the upper and lower sides for generating a static magnetic field along the perpendicular direction z, a bed part not shown in the drawings for inserting a subject (object of examination) into the static magnetic field within the body of the MRI device 500, a power supply section, a computer for calculating images etc. (processing unit, control unit), and so forth. Since the outline of the apparatus is the same as that of the block diagram shown in FIG. 2, explanation thereof is omitted.

As the bed part, the bed part 200 explained in Example 1 can be used, and the connection state (not shown in the drawing) of the bed part 200 and the body of the MRI device 500 is the same as that of Example 1. Further, as in Example 1, the bed part 200 is not limited to a dockable table, and a fixed bed may also of course be employed.

The main part of MRI device 500 comprises an upper body 502 containing the upper part of the magnet 501, a lower body 503 containing the lower part of the magnet 501, and a support part 504 that connects and supports the upper body 502 over the lower body 503. Between the upper body 502 and the lower body 503, a space of a predetermined size for inserting a test subject is formed, and a flat table surface 505 for inserting the test subject is formed on the upper surface of the lower body 503.

In this MRI device, an open-part 510 is formed between the upper body 502 and the lower body 503, and a position, at which the bed part not shown in the drawing is connected and fixed to, serves as the entrance of the open-part 510. In the example shown in FIG. 10, the entrance of the open-part is disposed at a position defined with a certain angle with respect to the straight line connecting the center of the supporting part 540 and the center of the table surface 503. However, the position of the entrance of the open-part is not limited to such a position as shown in the drawing.

One of the important features of the MRI device of this example is that a recessed entrance part 103 of the open-part provided around the entrance of the open-part 510, which entrance part 103 is formed with a gently curved surface that gradually retreats from the top surface 102 forwardly extruding from the circumference, and the entrance part 103 of the open-part formed at a position retreated from the top surface 102 is extended to a frontal lower part of the lower body 503.

Specifically, the upper body 502 comprises a circumferential panel serving as the upper surface thereof and the front panel 520 connected to the circumferential panel. The lower body 503 comprises a circumferential panel covering the upper surface except for the table surface 505, and the front panel 530 connected to the circumferential panel. The upper front panel 520 comprises an upper panel 521 at a position above the entrance of the open-part, and the lower front panel 530 comprises a lower panel 531 at a position under the entrance of the open-part. The front panel of this example except for the upper and lower panels corresponds to the outer panel of Example 1, and the upper and lower panels correspond to the inner panel of Example 1.

Panel connection parts at which the upper panel 521 and the lower panel 531 are connected with the front panels 520 and 530, respectively, constitute the forwardly protruding top surfaces 102, the upper panel 521 and the lower panel 531 are formed with mildly curved surfaces retreating from the top surfaces 102 so as to form recesses, and thereby a working space for the operator is secured. The upper panel or the lower panel and the front panel may not necessarily be constituted as separate members, and they may be formed as one body.

According to this example, a concave recessed part is formed from the vicinity of the opening to the ground plane, and therefore the recessed part can be used for access of the operator to the subject at the time of imaging.

Specifically, when the bed part is connected or fixed to the gantry part 500 of the aforementioned configuration, if the width of the tip part of the top panel base part supporting the top panel is not larger than the width of the top panel as shown in FIG. 6, the working space around the connection part becomes wider due to the presence of the recessed part of the front panel 521, and further becomes wider due to the thinner width of the top panel base part, and therefore workability of the operator is improved. Further, by disposing the lift of the bed part at a position shifted toward the side opposite to the connection part as shown in FIG. 5, there are given a space between the top panel base part and the base housing, and the space provided by the recessed part of the front panel 531 as a space in which the operator can move the legs, and therefore the degree of freedom for the motion of the legs increases.

DESCRIPTION OF NOTATIONS

1 . . . Subject, 2 . . . magnetic field generating system, 3 . . . gradient magnetic field generating system, 4 . . . sequencer, 5 . . . transmitting system, 6 . . . receiving system, 7 . . . signal-processing system, 8 . . . central processing unit (CPU), 9 . . . gradient coil, 10 . . . gradient magnetic field power supply, 11 . . . radio frequency oscillator, 12 . . . modulator, 13 . . . radio frequency amplifier, 14a . . . radio frequency coil (transmission coil), 14b . . . radio frequency coil (reception coil), 15 . . . signal amplifier, 16 . . . quadrature phase detector, 17 . . . A/D converter, 18 . . . magnetic disc, 19 . . . optical disc, 20 . . . display, 40 . . . magnet, 50 . . . operator, 51 . . . working space, 100 . . . gantry, 101 . . . bore (open-part), 102 . . . top surface, 103 . . . entrance part of bore, 104 . . . cylindrical member, 105 . . . recessed part, 106 . . . recessed orbital part, 110 . . . front panel, 111 . . . outer panel, 112 . . . inner panel, 113 . . . panel connection part, 120 . . . circumferential panel, 130 . . . back panel, 151 . . . operation panel, 152 . . . status display part, 200 . . . bed part, 201 . . . top panel, 202 . . . free wheel, 203 . . . base housing, 204 . . . top panel base part, 204a . . . end part, 205 . . . lift, 206 . . . handle, 207 . . . supporting surface, 208 . . . wheel supporting part, 300 . . . connection part, 310 . . . gantry-side connection part, 311 . . . connection housing, 312 . . . spring member, 313 . . . male connector, 350 . . . bed-side connection part, 350a . . . both sides of tip part, 350b . . . inside of tip part, 351 . . . female connector, 510 . . . open-part, 520, 530 . . . front panel, 521 . . . upper panel (inner panel), and 531 . . . lower panel (inner panel)

What is claimed is:

1. A magnetic resonance imaging device comprising:
a gantry containing a static magnetic field generating source for forming a static magnetic field space; and
a bed part having a top panel for placing a subject and inserting the subject into the static magnetic field space,
wherein the gantry includes a front panel having an opening serving as an entrance of an open-part for the static magnetic field space, and
at least a portion of the front panel around the opening is formed in a recessed shape,
wherein the front panel comprises an arc-shaped outer panel extending from a position above the opening and passing around both sides of the opening to a ground plane, and an inner panel disposed inside the arc-shaped outer panel, and
wherein a forwardly protruding top surface connects the outer panel and the inner panel, and the inner panel has a concave curved surface extending from the top surface to the opening to define the recessed shape of the front panel around the opening.

2. The magnetic resonance imaging device according to claim 1, wherein:
the bed part comprises a top panel base part on which a slidably movable top panel is provided, and
the top panel base part is formed with a width of an end part to be connected to the gantry not larger than the width of the top panel.

3. The magnetic resonance imaging device according to claim 1, wherein:
the bed part has a base housing provided with wheels for transfer,
the apparatus further comprises a connection part that enables attachment and detachment of the bed part to or from the gantry,
the connection part is constituted with a gantry-side connection part provided at the center of lower end part of the inner panel retreated backward from the top surface, and a bed-side connection part provided at one end side of the bed part for the longitudinal direction, and
the bed-side connection part is provided at the end of the base housing for the longitudinal direction.

4. The magnetic resonance imaging device according to claim 3, wherein:
the wheels for transfer are protrudingly provided on the both sides of the base housing for the transverse direction, and
when the bed part is connected to the gantry, the wheels for transfer exist on the both sides of the gantry-side connection part.

5. The magnetic resonance imaging device according to claim 1, wherein
the bed part comprises a base housing, a top panel base provided on the base housing and having a slidably movable top panel, and a lift ascendably and descendably supporting the top panel base,
a recessed part extending downward from the lower end of the opening is formed in the front panel, and the lift moves the top panel base up and down along the recessed part.

6. The magnetic resonance imaging device according to claim 5, wherein:
the lift of the bed part is disposed at a position shifted toward one side of the bed part remoter from the gantry for the longitudinal direction, and a space is formed between the top panel base and the base housing on the side nearer to the gantry.

7. The magnetic resonance imaging device according to claim 1, wherein:
the open-part for the static magnetic field space has a horizontal tunnel shape.

8. The magnetic resonance imaging device according to claim 1, wherein:
the static magnetic field generating source comprises a pair of magnet apparatuses oppositely disposed with an interval, and the open-part for the static magnetic field space is formed in a space between the pair of magnet apparatuses.

9. The magnetic resonance imaging device according to claim 8, wherein
the gantry has an upper front panel and a lower front panel, and
the upper front panel and the lower front panel each have a panel portion forming a recessed part in the vicinity of the entrance of the open-part.

10. The magnetic resonance imaging device according to claim 1, wherein
the bed part comprises a base housing, a top panel base provided on the base housing and having a slidably movable top panel, and a lift ascendably and descendably supporting the top panel base,
a recessed part extending downward from the lower end of the opening is formed in the front panel, and
the lift moves the top panel base up and down along the recessed part.

11. The magnetic resonance imaging device according to claim 1, wherein:
the open-part for the static magnetic field space has a horizontal tunnel shape.

* * * * *